(12) United States Patent
Raga et al.

(10) Patent No.: US 8,207,197 B2
(45) Date of Patent: Jun. 26, 2012

(54) MONOHYDROCHLORIDE SALT OF 1-[3-[3-(4-CHLOROPHENYL) PROPOXY] PROPYL]-PIPERIDINE

(75) Inventors: Manuel Raga, Barcelona (ES); Juan Sallares, Barcelona (ES); Marta Guerrero, Barcelona (ES); Antonio Guglietta, Molins de Rei (ES); Jean-Michel Arrang, Dourdan (FR); Jean-Charles Schwartz, Paris (FR); Holger Stark, Bad Homburg (DE); Walter Schunack, Berlin (DE); Xavier Ligneau, Saint Gregoire (FR); Jeanne-Marie Lecomte, Paris (FR); Charon Ganellin, Thame (GB)

(73) Assignee: Bioprojet, Paris (FR)

( * ) Notice: Subject to any disclaimer, the term of this patent is extended or adjusted under 35 U.S.C. 154(b) by 1115 days.

(21) Appl. No.: 11/815,736

(22) PCT Filed: Feb. 6, 2006

(86) PCT No.: PCT/EP2006/050703
§ 371 (c)(1),
(2), (4) Date: Mar. 27, 2008

(87) PCT Pub. No.: WO2006/084833
PCT Pub. Date: Aug. 17, 2006

(65) Prior Publication Data
US 2008/0221162 A1 Sep. 11, 2008

(30) Foreign Application Priority Data
Feb. 10, 2005 (EP) .................................... 05100942

(51) Int. Cl.
*A61K 31/4453* (2006.01)
*C07D 295/088* (2006.01)
(52) U.S. Cl. ........................ 514/317; 546/236
(58) Field of Classification Search .................. 514/317; 546/236
See application file for complete search history.

(56) References Cited

U.S. PATENT DOCUMENTS

| 7,138,413 | B1 * | 11/2006 | Schwartz et al. | ............. 514/312 |
| 7,169,928 | B2 * | 1/2007 | Schwartz et al. | ............. 546/236 |
| 7,910,605 | B2 * | 3/2011 | Schwartz et al. | ............. 514/317 |

FOREIGN PATENT DOCUMENTS

| EP | 0 982 300 | 3/2000 |
| EP | 1 428 820 | 6/2004 |

OTHER PUBLICATIONS

Berge et al. "Pharmaceutical salts" J. Pharm Sci. v.66(1) p. 1-19 (1977).*
Borchardt et al. :Pharm. profiling . . . p. 93-125 (2004).*
Braga et al. "Making crystals . . . " J. Roy. soc. Chem. Chem. Commun. p. 3635-3645 (2005).*
Cheronis "Purification of solids by crystallization" Semimicro. Exp. Org. Chem. p. 31-43 (1958).*
Dean "analyticl Chem. Handbook" p. 10-24-10.26 (1995).*
Doward "Side reactions . . . " p. ix (2005).*
Hammond et al. "Grid based molecular . . . " J. Pharm. Sci, v.95(11) p. 2361-2372 (2006).*
Kirk-Othmer "Crystallization" Encyclopedia of Chem. Tech. p. 95-147 (2002).*
Seddon "Pseudopolymorph . . . " Crystal grow & design vol. 4(6) p. 1087 (two pages form internet).*
Trask et al. "Screening for crystalline . . . " Roy. Soc, Chem. Chem. Commun. p. 51-53 (2006).*
Vippagunta et al. "Crystalline solids" Adv. Drg. Del. Rev. v.48, p. 3-26 (2001).*
Meier Galina et al, "Influence of imidazole replacement in different structural classes of histamine H3-receptor antagonists", Jun. 2001, pp. 249-259, vol. 13, No. 3, European Journal of Pharmaceutical Sciences, Elsevier, Amsterdam, Netherlands.

* cited by examiner

*Primary Examiner* — Celia Chang
(74) *Attorney, Agent, or Firm* — B. Aaron Schulman, Esq.; Stites & Harbison PLLC

(57) ABSTRACT

The invention relates to new crystalline 1-[3-[3-(4-chlorophenyl)propoxy]propyl]-piperidine monohydrochloride, the respective manufacture and methods of use, and compositions containing such a compound.

10 Claims, 1 Drawing Sheet

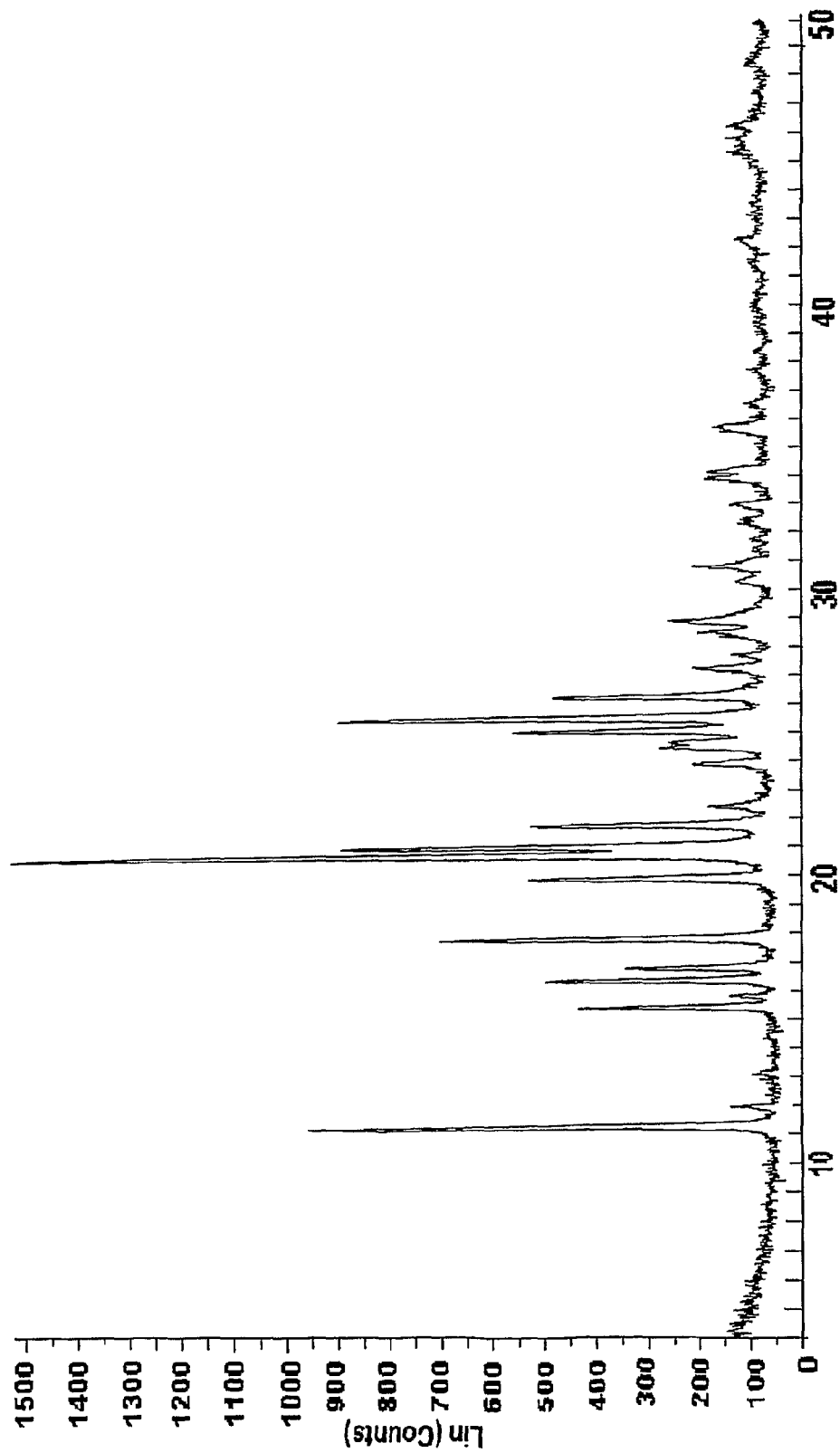

MONOHYDROCHLORIDE SALT OF 1-[3-[3-(4-CHLOROPHENYL) PROPOXY] PROPYL] -PIPERIDINE

The present invention relates to a novel compound, to the process for preparing it, to pharmaceutical compositions comprising it and to its use in treating medical disorders.

BACKGROUND ART

Pharmaceutical products with histamine H3 receptor ligand properties and subsequent pharmacological activities thereof are described in EP-980300. An especially important product among those disclosed is 1-[3-[3-(4-chlorophenyl) propoxy]propyl]-piperidine. This compound is disclosed as the free base and as the oxalate salt.

The use of 1-[3-[3-(4-chlorophenyl)propoxy]propyl]-piperidine as the free base is limited because of its oily nature. On the contrary, 1-[3-[3-(4-chlorophenyl)propoxy]propyl]-piperidine oxalate is a crystalline substance but its low aqueous solubility (0.025 g/ml at 23° C.) also limits its use as a pharmaceutical ingredient.

Subsequent patents EP-1100503 and EP-1428820 mention certain salts of 1-[3-[3-(4-chlorophenyl)propoxy]propyl]-piperidine. However, the only one specifically described is the oxalate salt. The crystalline monohydrochloride salt is not described.

SUMMARY OF THE INVENTION

We have now surprisingly discovered a novel salt of 1-[3-[3-(4-chlorophenyl)propoxy]propyl]-piperidine which may be used as an alternative to the currently described free base and oxalate.

An aspect of the invention provides the crystalline 1-[3-[3-(4-chlorophenyl)propoxy]propyl]-piperidine monohydrochloride of formula (I)

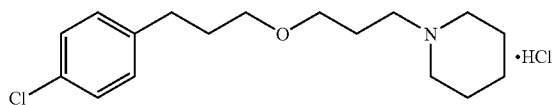

(I)

and its pharmaceutically acceptable solvates, including hydrates

The compound (I) has a maximum water content of 6±0.5% and shows characteristic IR peaks at 1112, 1101, 2936, 2868, 1455, 2647, 2551, 1492, and 802±5 cm$^{-1}$.

The crystalline 1-[3-[3-(4-chlorophenyl)propoxy]propyl]-piperidine monohydrochloride as claimed herein has an X-ray powder diffraction pattern with characteristic peaks (2θ): 11.2°, 19.9°, 20.7° and 34.1° (±0.2°) as shown in the experimental data included in Example 3.

The aqueous solubility of crystalline 1-[3-[3-(4-chlorophenyl)propoxy]propyl]-piperidine monohydrochloride (4 g/ml at 23° C.) is unexpectedly much higher than the aqueous solubility of the oxalate salt. Furthermore, the monohydrochloride salt shows better profile of stability to oxidation conditions than other salts. as shown in the experimental data included in Example 4. Therefore, crystalline 1-[3-[3-(4-chlorophenyl)propoxy]propyl]-piperidine monohydrochloride has proved to be a more suitable salt for its use as a pharmaceutical ingredient Crystalline 1-[3-[3-(4-chlorophenyl)propoxy]propyl]-piperidine monohydrochloride may show a variable content of water. However, the X-ray diffraction pattern obtained from different samples indicates that all samples correspond to the same crystal structure, except for small variations related to different water contents, as shown in Example 3, Table 2.

According to the experimental studies, water content in the 1-[3-[3-(4-chlorophenyl)propoxy]propyl]-piperidine monohydrochloride crystals ranges from traces to 6±0.5%.

In another aspect the present invention provides a process for the preparation of crystalline 1-[3-[3-(4-chlorophenyl)propoxy]propyl]-piperidine monohydrochloride by reacting the free base product with a reactant selected from hydrogen chloride and hydrochloric acid in a suitable solvent and isolating the precipitated final product. The reaction occurs fairly at room temperature. Preferably, the reactant is hydrogen chloride. More preferably, the hydrogen chloride is added as gaseous hydrogen chloride.

The suitable solvent is selected from the group consisting of acetone, methanol, ethanol, propanol, water, ethyl acetate, i-propanol, butanol, i-butanol, s-butanol, t-butanol, hexane, toluene, t-butyl-methyl ether, trichloroethane and the like, and mixtures thereof. Preferably, the solvent is ethyl acetate.

The precipitation of the end product may be performed by cooling the mass reaction. A suitable temperature for this operation is from 0 to −15° C.

The precipitated final product can be isolated by some different common techniques used in organic chemistry. The most preferred is filtration.

The isolated final product can be purified by some different habitual techniques of organic chemistry. The most preferred is crystallization.

The suitable solvent used in the crystallization step is selected from the group consisting of acetone, methanol, ethanol, propanol, water, ethyl acetate, i-propanol, butanol, i-butanol, s-butanol, t-butanol, hexane, toluene, t-butyl-methyl ether, trichloroethane and the like, and mixtures thereof. Preferably, the suitable solvent used in the crystallization step is a mixture of ethyl acetate and i-propanol.

According to another aspect, the invention provides a method for the treatment of a human suffering from central nervous system disorders, such as epilepsy Alzheimer's disease and attention, wakefulness and memorization disorders, cognitive deficits in psychiatric pathologies disorders in aged persons, depressive and asthenic states, and vertigo and motion sickness, said method comprising the administration of a therapeutically effective amount of the crystalline 1-[3-[3-(4-chlorophenyl)propoxy]propyl]-piperidine monohydrochloride of formula (I) together with pharmaceutically acceptable diluents or carriers, to said patient. This aspect of the invention may alternatively be formulated as the use of the crystalline 1-[3-[3-(4-chlorophenyl)propoxy]propyl]-piperidine monohydrochloride for the manufacture of a medicament for the treatment of the diseases mentioned above.

In another aspect, the invention provides a method for the treatment of obesity, said method comprising the administration of a therapeutically effective amount of the crystalline 1-[3-[3-(4-chlorophenyl)propoxy]propyl]-piperidine monohydrochloride of formula (I) together with pharmaceutically acceptable diluents or carriers, to said patient. This aspect of the invention may alternatively be formulated as the use of the crystalline 1-[3-[3-(4-chlorophenyl)propoxy]propyl]-piperidine monohydrochloride for the manufacture of a medicament for the treatment of obesity.

In another aspect, the invention provides a method for the treatment of psychosomatic disorders, respiratory, allergic conditions, inflammatory conditions, cardiac conditions, gastrointestinal conditions, conditions of the urogenital system and conditions of the cutaneous system, such as sleep disorders, sleep apnea, sleep induced apnea, diurnal somnolence, stress, migraine, headache, pain, psychotropic disorders, asthma, bronchitis, rhinitis, tracheitis, gastric ulcers, duodenal ulcers, ulcerative colitis, Crohn's disease, irritable bowel syndrome, cystitis, metritis, urinary and fecal incontinence, urticaria, itching, arthritis, conjunctivitis, premenstrual syndrome, prostatic inflammations, genital disorders, rheumatic and ocular conditions, sialorrhea, convulsion, depression, disorders of the hypothalamohypophyseal secretion, the cerebral circulation and the immune system, said method comprising the administration of a therapeutically effective amount of the crystalline 1-[3-[3-(4-chlorophenyl)propoxy]propyl]-piperidine monohydrochloride of formula (I) together with pharmaceutically acceptable diluents or carriers, to said patient. This aspect of the invention may alternatively be formulated as the use of the crystalline 1-[3-[3-(4-chlorophenyl)propoxy]propyl]-piperidine monohydrochloride for the manufacture of a medicament for the treatment of the diseases mentioned above.

According to the present invention, the term "treatment" encompasses both treatment and prophylaxis of diseases or pathologic conditions.

According to another aspect, the invention provides a method for the prevention of the undesirable side effects associated with antipsychotic or antidepressant agents. Antipsychotic agent refers to aripiprazole, clozapine, olanzapine, risperidone, quetiapine, and sertindole, and the like; antidepressant agent refers to mirtazapine, amitryptiline and paroxetine, and the like. The undesirable side effects associated with antipsychotic or antidepressant agents include weight gain, somnolence and cognitive impairment.

The compositions of this invention are usually adapted for oral administration, but formulations for dissolution of parenteral administration are also within the scope of this invention.

The composition is usually presented as a unit-dose composition containing from 1 to 200 mg of active ingredient, more usually from 5 to 100 mg, for example 10 to 50 mg such as 10, 12.5, 15, 20, 25, 30 or 40 mg for a human patient. Most preferably unit doses contain 20 or 40 mg of active ingredient. Such a composition is normally taken from 1 to 6 times daily, for example 2, 3 or 4 times daily so that the total amount of active agent administered is within the range of from 5 to 400 mg of active ingredient. Thus a suitable daily dose is from 0.05 to 6 mg/kg, more preferably 0.14 to 0.86 mg/kg.

Preferred unit dosage forms include tablets, coated tablets, capsules and oral solutions. More preferred forms are coated tablets.

In another aspect the invention provides compositions comprising 1-[3-[3-(4-chlorophenyl)propoxy]propyl]-piperidine monohydrochloride as an active ingredient.

In another aspect the invention also provides compositions further comprising an antipsychotic or antidepressant agent. Representative antipsychotic agents are selected from the group consisting of aripiprazole, clozapine, olanzapine, risperidone, quetiapine, and sertindole; and representative antidepressant agents are selected from the group consisting of mirtazapine, amitryptiline and paroxetine.

In compositions comprising an antipsychotic or antidepressant agent and the compound of the present invention, the quantities of antipsychotic or antidepressant agent stand for usual therapeutic doses, being 1-[3-[3-(4-chlorophenyl)propoxy]propyl]-piperidine monohydrochloride in sufficient dose ranges to counteract at least one of the three undesirable side effects of the psychotropic medication namely, weight gain, somnolence and memory impairment. Examples of preparations include the compound of the present invention in a range of doses from about 5 to about 80 mg, and a) olanzapine from about 3 to about 20 mg, b) risperidone from about 0.5 to about 10 mg, c) aripiprazole from about 10 to about 30 mg or d) mirtazapine from about 15 to about 45 mg.

The compositions of this invention may be formulated by conventional methods of admixture such as blending, filling, compressing and coating.

Suitable carriers for use in this invention include a diluent, a binder, a disintegrant, a lubricant and a glidant. Further the composition comprises a film coating polymer.

The diluent is selected from the group comprising calcium phosphate, dicalcium phosphate, tricalcium phosphate, calcium sulfate, anhydrous lactose, spray dried lactose, hydrated lactose, cellulose, spray dried microcrystalline cellulose, spray dried combinations comprising microcrystalline cellulose and lactose, silicified microcrystalline cellulose, kaolin, bentonite, mannitol, starch, magnesium carbonate, sorbitol, sucrose, inositol, compressible sugar, threalose and xilitol, and mixtures thereof. The diluent total weight ranges from 20 to 90%.

The binder is selected from the group comprising acacia, microcrystalline cellulose, cellulosic solutions such as hydroxypropylmethylcellulose, gelatin solutions 10-20%, glucose solutions 20-50%, polyvinylpyrrolidone, starch paste 10-20%, sorbitol, tragacanth, polyethyleneglycol, maltodextrin, polymethacrylates and povydone, and mixtures thereof. The binder total maximum weight is around 20%.

The disintegrant is selected from the group comprising corn starch, potato starch, methylcellulose, cellulose, carboxymethylcellulose or salts thereof, such as carboxymethylcellulose calcium salt, mineral clay powders, bentonite/veegum, wetting agents such as sodium lauryl sulfate, superdisintegrants (named due to low concentration needed, i.e. 2-4%), croscarmellose, crospovidone and sodium starch glycolate, and mixtures thereof. The disintegrant total weight ranges from 2 to 5%.

The lubricant is selected from the group comprising polyethyleneglycol, poloxamer, magnesium stearate at concentration under 1%, calcium stearate, stearic acid, hydrogenated vegetable oils, talc and glyceryl behenate, and mixtures thereof. The lubricant total maximum weight is around 5%.

The glidant is selected from the group comprising colloidal silicon dioxide, talc and corn starch, and mixtures thereof. The glidant total weight ranges from 0.1 to 1%.

The film coated polymer is selected from the group comprising acrylic acid polymer, preferably basic butylated methacrylate copolymer, cellulose derivatives such as hydroxypropylcellulose, hydroxypropylmethylcellulose, methylcellulose, hydroxyethylcellulose and the like, polyvinyl alcohol and mixtures thereof with polysaccharides, and mixtures thereof.

Examples of coating polymer suspensions comprise basic butylated methacrylate copolymer, sodium lauryl sulfate, stearic acid and purified water.

Film coating polymers also include plasticizers, lubricants and pigments when necessary.

Examples of pigment suspensions comprise talc, titanium dioxide, magnesium stearate and purified water.

Throughout the description and claims the word "comprise" and variations of the word, such as "comprising", is not intended to exclude other technical features, additives, components, or steps.

Additional objects, advantages and features of the invention will become apparent to those skilled in the art upon examination of the description or may be learned by practice of the invention. The following examples are provided by way of illustration, and are not intended to be limiting of the present invention.

BRIEF DESCRIPTION OF DRAWINGS

FIG. 1 shows an X-ray diffraction pattern of crystalline 1-[3-[3-(4 chlorophenyl)propoxy]propyl]-piperidine monohydrochloride.

DETAILED DESCRIPTION OF PARTICULAR EMBODIMENTS

Example 1

1-[3-[3-(4-chlorophenyl)propoxy]propyl]-piperidine

According to the method disclosed in EP-982300, Example 78, sodium 3-piperidinopropanolate (2.127 kg; 12.88 mol), 3-(4-chlorophenyl)propyl mesylate (1.121 kg; 4.51 mol) and 0.322 mol of 15-crown-5 in 4.5 kg of dry toluene were refluxed for 4 hours. The solvent was evaporated and the residue purified by column chromatography on silica gel (eluent: methylene chloride/methanol (90/10)). The obtained oil was distilled in a fractionating equipment at reduced pressure (0.3-0.7 mmHg) and with a heating jacket at 207-210° C. The head fractions and the distilled fraction at 0.001-0.010 mmHg with a jacket temperature of 180-200° C. were collected. The obtained oil (1.0 kg; 3.38 mol) corresponds to 1-[3-[3-(4-chlorophenyl)propoxy]propyl]-piperidine. Yield 75%.

Example 2

1-[3-[3-(4-chlorophenyl)propoxy]propyl]-piperidine monohydrochloride

Preparation

Distilled 1-[3-[3-(4-chlorophenyl)propoxy]propyl]-piperidine (1.0 kg) and anhydrous ethyl acetate (4.5 kg) are transferred to a 10-L glass vessel fitted with a cooling bath and a gas inlet. A stream of gaseous hydrogen chloride is bubbled in the reaction mixture at 20-25° C.

The pH of the solution is checked by taking a 0.5 mL sample of the reaction mixture and diluting it with 5 mL of deionized water. The final pH must be about 3-4.

The mixture is cooled to −10° C.-(−12° C.) and stirred at this temperature for 1 h. The precipitate is filtered by using a sintered glass filter and washed with 0.5 L of anhydrous ethyl acetate previously cooled to 0-5° C. The product is dried in a vacuum oven at 50° C. for a minimum period of 12 hours. The resulting crude 1-[3-[3-(4-chlorophenyl)propoxy]propyl]-piperidine monohydrochloride weighs 1.10 kg.

Purification

A mixture of the above-described crude, 3.98 kg of anhydrous ethyl acetate and 0.35 kg of i-propanol is heated slowly at 55-60° C. in a 10-L glass vessel fitted with a heating and cooling system. When the solution has been completed, it is filtered through a heat-isolated sintered glass filter, keeping the temperature at 55-60° C. The solution is transferred to a 10 L glass vessel and the mass is slowly cooled to 0-5° C. for about 1 hour. The mixture is stirred at this temperature for 1 hour and the precipitate is filtered through a sintered glass filter. The solid is washed with a mixture of 1.6 kg of anhydrous ethyl acetate and 0.14 kg of i-propanol cooled at 0-5° C. The solid is dried in a vacuum oven at 50° C. for a minimum period of 12 hours. M.p. 117-119° C. Yield 80%.

IR spectrum (KBr): bands at 1112 and 1101 (C—O Ether/ St. asym), 2936 and 2868 (Alkane $CH(CH_2)$/St.), 1455 (Alkane $CH(CH_2)$/Deform.), 2647 and 2551 (Amine Salt/St.), 1492 (Amine/St.), 802 (Aromatic/Deform.) $cm^{-1}$.

Example 3

X-Ray Diffraction Studies

Crystal data were obtained using a Nonius Kappa Charge Coupled Device system at −158° C. The used wavelength was 0.71073 Å. The crystal structure was solved by direct methods and refined by means of SHELX97 in the WinGX package environment.

It was discovered that crystalline 1-[3-[3-(4-chlorophenyl) propoxy]propyl]-piperidine monohydrochloride may show a variable content of water. However, all analyzed samples exhibit the same crystal structure, independently of the water content. According to the experimental studies, water content in the 1-[3-[3-(4-chlorophenyl)propoxy]propyl]-piperidine monohydrochloride crystals can reach up to 6±0.5%.

A summary of the crystal data and data refinement parameters for a sample containing a water content of 2.7% is shown in Table 1.

TABLE 1

Crystal data parameters for 1-[3-[3-(4-chlorophenyl)propoxy]propyl]-piperidine monohydrochloride

| | | |
|---|---|---|
| Crystal system | Monoclinic | |
| Space group | $P2_1$ | |
| Unit cell dimensions | a = 14.1588(8)Å | $\alpha = 90°$ |
| | b = 8.2798(6)Å | $\beta = 97.996(4)°$ |
| | c = 15.9262(13)Å | $\gamma = 90°$ |
| Volume | 1848.9(2)Å3 | |
| Z | 4 | |
| Density (calculated) | 1.226 g/cm3 | |
| Absorption coefficient | 0.354 $mm^{-1}$ | |
| F(000) | 732 | |
| Crystal size | 0.25 × 0.10 × 0.05 $mm^3$ | |
| Theta range for data collection | 1.80 to 25.95° | |
| Index ranges | −17 <= h <= 17, −9 <= k <= 10, −19 <= l <= 19 | |
| Reflections collected | 6442 | |
| Independent reflections | 6442 | |
| Completeness to $\theta = 25.95°$ | 98.2% | |
| Max. and min. transmission | 0.9825 and 0.9167 | |

Two sites partially occupied with water molecules are localized in the asymmetric unit (also containing two principle molecules).

The volume available for each water molecule is about 15 $Å^3$, which is lower than the usually assumed value of 40 $Å^3$.

Due to competitive mechanisms (water hydrogen bonds linking principle molecules vs. a low void volume available for water molecules), crystal structures are partially disordered giving rise to a rationale about the ability of the structure to accommodate different proportions of water molecules without changing the structure. The crystal packing is stabilized by the connections N1-H . . . Cl2H-Ow-H . . . O1. From unit cell fittings of powder X-ray diffraction patterns of samples with different water content, it is observed that cell parameters (a, b, c, V) decrease slightly with increasing proportions of water in the structure, as shown in Table 2.

TABLE 2

Comparative crystal parameters for 1-[3-[3-(4-chlorophenyl)propoxy]propyl]-piperidine monohydrochloride depending on the water content

| Parameter | 2.7% H$_2$O | 2.8% H$_2$O | 3.7% H$_2$O | 6.0% H$_2$O |
|---|---|---|---|---|
| a(Å) | 14.1588(8) | 14.279(7) | 14.24(3) | 14.202(3) |
| b(Å) | 8.2798(6) | 8.450(4) | 8.40(1) | 8.368(14) |
| c(Å) | 15.9262(13) | 15.872(5) | 15.98(3) | 15.69(6) |
| β(°) | 97.996(4) | 97.11(7) | 96.9(3) | 97.1(4) |
| Volume (Å$^3$) | 1848.9(2) | 1900(1) | 1897(5) | 1850(6) |
| Density (g/cm$^3$) | 1226 | 1195 | 1208 | 1269 |

In summary, the X-ray diffraction pattern obtained from different samples indicates that all samples correspond to the same crystal structure, except for small variations related to different water contents.

Atomic coordinates for the crystal structure are shown in Table 3. Bond lengths and angles are shown in Table 4. Torsion angles are shown in Table 5.

TABLE 3

Atomic coordinates (×10$^4$) and equivalent isotropic displacement parameters (Å$^2$ × 10$^3$) for the 1-[3-[3-(4-chlorophenyl)propoxy]propyl]-piperidine monohydrochloride crystal. U(eq) is defined as one third of the trace of the orthogonalized U$^{ij}$ tensor.

| | x | y | z | U(eq) |
|---|---|---|---|---|
| Cl(1A) | −8054(2) | −621(4) | 26062(2) | 80(1) |
| Cl(2A) | −1644(1) | 1125(3) | 19286(1) | 48(1) |
| N(1A) | −3754(4) | 1279(10) | 19534(4) | 36(2) |
| O(1A) | −3879(4) | 997(8) | 22251(3) | 51(2) |
| C(1A) | −7122(6) | −147(11) | 25500(6) | 43(3) |
| C(2A) | −7141(7) | −689(13) | 24681(6) | 53(3) |
| C(3A) | −6394(6) | 782(12) | 25912(6) | 55(3) |
| C(4A) | −6365(7) | −224(12) | 24272(6) | 52(3) |
| C(5A) | −5662(7) | 1159(15) | 25488(6) | 63(3) |
| C(6A) | −5634(6) | 756(15) | 24658(7) | 68(4) |
| C(7A) | −4824(6) | 1528(14) | 24251(4) | 99(5) |
| C(8A) | −4788(5) | 992(15) | 23378(5) | 80(4) |
| C(9A) | −3942(5) | 1756(12) | 23060(5) | 60(3) |
| C(10A) | −3024(6) | 1457(14) | 21934(5) | 63(3) |
| C(11A) | −3054(6) | 913(16) | 21049(5) | 66(3) |
| C(12A) | −3797(6) | 1721(12) | 20443(5) | 49(3) |
| C(13A) | −4146(6) | −356(12) | 19320(6) | 49(3) |
| C(14A) | −4237(6) | 2556(12) | 18965(7) | 58(3) |
| C(15A) | −4074(7) | −775(15) | 18434(6) | 59(3) |
| C(16A) | −4210(7) | 2112(16) | 18022(7) | 76(4) |
| C(17A) | −4558(7) | 452(15) | 17824(7) | 62(3) |
| Cl(1B) | −3025(2) | −165(4) | 16127(2) | 89(1) |
| Cl(2B) | 3363(1) | 1135(3) | 9394(1) | 46(1) |
| N(1B) | 1240(4) | 1338(9) | 9620(4) | 37(2) |
| O(1B) | 1038(4) | 1092(9) | 12356(3) | 51(2) |
| C(1B) | −2099(7) | −22(12) | 15520(7) | 50(3) |
| C(2B) | −2188(7) | −753(12) | 14747(7) | 53(3) |
| C(3B) | −1296(6) | 885(13) | 15800(5) | 47(3) |
| C(4B) | −1477(8) | −674(14) | 14248(6) | 64(3) |
| C(5B) | −578(5) | 932(12) | 15283(6) | 46(2) |
| C(6B) | −670(6) | 174(14) | 14510(5) | 53(3) |
| C(7B) | 156(6) | 288(14) | 13969(7) | 70(4) |
| C(8B) | 149(6) | 1757(12) | 13510(6) | 55(3) |
| C(9B) | 1030(6) | 2067(13) | 13088(5) | 52(3) |
| C(10B) | 1915(6) | 1312(16) | 12029(5) | 66(3) |
| C(11B) | 1859(6) | 765(15) | 11136(5) | 67(4) |
| C(12B) | 1161(6) | 1702(12) | 10535(5) | 50(3) |
| C(13B) | 841(6) | −245(10) | 9310(6) | 41(3) |
| C(14B) | 767(6) | 2702(12) | 9107(7) | 49(3) |
| C(15B) | 942(7) | −507(15) | 8398(6) | 72(4) |
| C(16B) | 849(7) | 2475(16) | 8169(8) | 85(4) |
| C(17B) | 470(5) | 861(10) | 7871(4) | 84(5) |
| OW1A | 3255(5) | 2735(10) | 7546(4) | 65(5) |
| OW1B | 8282(5) | 2842(10) | 7425(4) | 103(8) |

TABLE 4

Bond lengths [Å] and angles [°] for the 1-[3-[3-(4-chlorophenyl)propoxy]propyl]-piperidine monohydrochloride crystal

| Cl(1A)-C(1A) | 1.739(8) |
|---|---|
| N(1A)-C(13A) | 1.485(11) |
| N(1A)-C(14A) | 1.496(11) |
| N(1A)-C(12A) | 1.503(10) |
| O(1A)-C(10A) | 1.426(9) |
| O(1A)-C(9A) | 1.447(9) |
| C(1A)-C(2A) | 1.376(12) |
| C(1A)-C(3A) | 1.376(12) |
| C(2A)-C(4A) | 1.406(12) |
| C(3A)-C(5A) | 1.350(12) |
| C(4A)-C(6A) | 1.389(14) |
| C(5A)-C(6A) | 1.369(13) |
| C(6A)-C(7A) | 1.533(11) |
| C(7A)-C(8A) | 1.467(5) |
| C(8A)-C(9A) | 1.504(5) |
| C(10A)-C(11A) | 1.475(11) |
| C(11A)-C(12A) | 1.485(11) |
| C(13A)-C(15A) | 1.470(11) |
| C(14A)-C(16A) | 1.552(13) |
| C(15A)-C(17A) | 1.503(13) |
| .(16A)-C(17A) | 1.479(14) |
| Cl(1B)-C(1B) | 1.739(9) |
| N(1B)-C(13B) | 1.483(10) |
| N(1B)-C(14B) | 1.496(11) |
| N(1B)-C(12B) | 1.508(9) |
| O(1B)-C(9B) | 1.419(9) |
| O(1B)-C(10B) | 1.423(9) |
| C(1B)-C(2B) | 1.362(12) |
| C(1B)-C(3B) | 1.384(12) |
| C(2B)-C(4B) | 1.369(13) |
| C(3B)-C(5B) | 1.395(10) |
| .(4B)-C(6B) | 1.356(13) |
| C(5B)-C(6B) | 1.372(12) |
| C(6B)-C(7B) | 1.550(11) |
| C(7B)-C(8B) | 1.418(11) |
| C(8B)-C(9B) | 1.519(10) |
| C(10B)-C(11B) | 1.484(11) |
| C(11B)-C(12B) | 1.495(11) |
| C(13B)-C(15B) | 1.495(11) |
| C(14B)-C(16B) | 1.526(14) |
| C(15B)-C(17B) | 1.509(13) |
| C(16B)-C(17B) | 1.493(14) |
| C(13A)-N(1A)-C(14A) | 112.3(7) |
| C(13A)-N(1A)-C(12A) | 112.3(7) |
| C(14A)-N(1A)-C(12A) | 109.6(7) |
| C(10A)-O(1A)-C(9A) | 111.1(6) |
| C(2A)-C(1A)-C(3A) | 123.2(8) |
| C(2A)-C(1A)-Cl(1A) | 119.9(7) |
| C(3A)-C(1A)-Cl(1A) | 116.9(7) |
| C(1A)-C(2A)-C(4A) | 115.9(9) |
| C(5A)-C(3A)-C(1A) | 117.9(9) |
| C(6A)-C(4A)-C(2A) | 122.5(9) |
| C(3A)-C(5A)-C(6A) | 123.6(10) |
| C(5A)-C(6A)-C(4A) | 116.7(9) |
| C(5A)-C(6A)-C(7A) | 115.5(10) |
| C(4A)-C(6A)-C(7A) | 127.7(9) |
| C(8A)-C(7A)-C(6A) | 113.6(8) |
| C(7A)-C(8A)-C(9A) | 109.1(5) |
| O(1A)-C(9A)-C(8A) | 105.6(6) |
| O(1A)-C(10A)-C(11A) | 110.1(8) |
| C(10A)-C(11A)-C(12A) | 114.0(8) |
| C(11A)-C(12A)-N(1A) | 113.3(7) |
| C(15A)-C(13A)-N(1A) | 111.2(8) |
| N(1A)-C(14A)-C(16A) | 110.4(8) |
| C(13A)-C(15A)-C(17A) | 112.0(9) |
| C(17A)-C(16A)-C(14A) | 112.0(9) |
| C(16A)-C(17A)-C(15A) | 112.5(10) |
| C(13B)-N(1B)-C(14B) | 111.4(6) |
| C(13B)-N(1B)-C(12B) | 114.9(7) |
| C(14B)-N(1B)-C(12B) | 106.8(7) |
| C(9B)-O(1B)-C(10B) | 109.6(6) |
| C(2B)-C(1B)-C(3B) | 120.2(8) |
| C(2B)-C(1B)-Cl(1B) | 119.3(8) |
| C(3B)-C(1B)-Cl(1B) | 120.5(8) |
| C(1B)-C(2B)-C(4B) | 121.3(10) |
| C(1B)-C(3B)-C(5B) | 117.2(8) |
| C(6B)-C(4B)-C(2B) | 120.1(10) |

TABLE 4-continued

Bond lengths [Å] and angles [°] for the 1-[3-[3-(4-chlorophenyl)propoxy]propyl]-piperidine monohydrochloride crystal

| | |
|---|---|
| C(6B)-C(5B)-C(3B) | 122.1(8) |
| C(4B)-C(6B)-C(5B) | 119.0(8) |
| C(4B)-C(6B)-C(7B) | 121.9(10) |
| C(5B)-C(6B)-C(7B) | 119.1(9) |
| C(8B)-C(7B)-C(6B) | 112.7(8) |
| C(7B)-C(8B)-C(9B) | 115.1(8) |
| O(1B)-C(9B)-C(8B) | 111.6(7) |
| O(1B)-C(10B)-C(11B) | 112.3(7) |
| C(10B)-C(11B)-C(12B) | 113.5(9) |
| C(11B)-C(12B)-N(1B) | 112.6(7) |
| N(1B)-C(13B)-C(15B) | 111.5(8) |
| N(1B)-C(14B)-C(16B) | 110.6(8) |
| C(13B)-C(15B)-C(17B) | 109.7(8) |
| C(17B)-C(16B)-C(14B) | 110.4(8) |
| C(16B)-C(17B)-C(15B) | 112.5(7) |

TABLE 5

Torsion angles [°] for the 1-[3-[3-(4-chlorophenyl)propoxy]propyl]-piperidine monohydrochloride crystal

| | |
|---|---|
| C(3A)-C(1A)-C(2A)-C(4A) | −0.6(14) |
| Cl(1A)-C(1A)-C(2A)-C(4A) | 178.9(7) |
| C(2A)-C(1A)-C(3A)-C(5A) | −0.7(14) |
| Cl(1A)-C(1A)-C(3A)-C(5A) | 179.8(8) |
| C(1A)-C(2A)-C(4A)-C(6A) | −1.6(15) |
| C(1A)-C(3A)-C(5A)-C(6A) | 4.3(17) |
| C(3A)-C(5A)-C(6A)-C(4A) | −6.3(17) |
| C(3A)-C(5A)-C(6A)-C(7A) | 170.4(10) |
| C(2A)-C(4A)-C(6A)-C(5A) | 4.8(16) |
| C(2A)-C(4A)-C(6A)-C(7A) | −171.4(10) |
| C(5A)-C(6A)-C(7A)-C(8A) | 176.7(11) |
| C(4A)-C(6A)-C(7A)-C(8A) | −7.1(17) |
| C(6A)-C(7A)-C(8A)-C(9A) | −177.2(10) |
| C(10A)-O(1A)-C(9A)-C(8A) | −172.0(9) |
| C(7A)-C(8A)-C(9A)-O(1A) | 172.1(9) |
| C(9A)-O(1A)-C(10A)-C(11A) | −169.9(9) |
| O(1A)-C(10A)-C(11A)-C(12A) | 66.0(13) |
| C(10A)-C(11A)-C(12A)-N(1A) | 174.2(9) |
| C(13A)-N(1A)-C(12A)-C(11A) | 76.2(9) |
| C(14A)-N(1A)-C(12A)-C(11A) | −158.2(8) |
| C(14A)-N(1A)-C(13A)-C(15A) | 57.4(9) |
| C(12A)-N(1A)-C(13A)-C(15A) | −178.6(7) |
| C(13A)-N(1A)-C(14A)-C(16A) | −53.8(9) |
| C(12A)-N(1A)-C(14A)-C(16A) | −179.4(7) |
| N(1A)-C(13A)-C(15A)-C(17A) | −56.3(11) |
| N(1A)-C(14A)-C(16A)-C(17A) | 51.0(11) |
| C(14A)-C(16A)-C(17A)-C(15A) | −51.2(11) |
| C(13A)-C(15A)-C(17A)-C(16A) | 54.2(12) |
| C(3B)-C(1B)-C(2B)-C(4B) | 3.0(15) |
| Cl(1B)-C(1B)-C(2B)-C(4B) | −179.9(8) |
| C(2B)-C(1B)-C(3B)-C(5B) | −3.6(14) |
| Cl(1B)-C(1B)-C(3B)-C(5B) | 179.4(7) |
| C(1B)-C(2B)-C(4B)-C(6B) | −1.5(17) |
| C(1B)-C(3B)-C(5B)-C(6B) | 2.8(14) |
| C(2B)-C(4B)-C(6B)-C(5B) | 0.6(16) |
| C(2B)-C(4B)-C(6B)-C(7B) | 179.9(9) |
| C(3B)-C(5B)-C(6B)-C(4B) | −1.4(15) |
| C(3B)-C(5B)-C(6B)-C(7B) | 179.6(8) |
| C(4B)-C(6B)-C(7B)-C(8B) | 99.9(13) |
| C(5B)-C(6B)-C(7B)-C(8B) | −81.1(12) |
| C(6B)-C(7B)-C(8B)-C(9B) | 170.0(9) |
| C(10B)-O(1B)-C(9B)-C(8B) | −174.6(8) |
| C(7B)-C(8B)-C(9B)-O(1B) | 74.7(11) |
| C(9B)-O(1B)-C(10B)-C(11B) | −161.8(9) |
| O(1B)-C(10B)-C(11B)-C(12B) | 63.2(13) |
| C(10B)-C(11B)-C(12B)-N(1B) | 169.7(8) |
| C(13B)-N(1B)-C(12B)-C(11B) | 74.7(9) |
| C(14B)-N(1B)-C(12B)-C(11B) | −161.2(8) |
| C(14B)-N(1B)-C(13B)-C(15B) | 58.0(9) |
| C(12B)-N(1B)-C(13B)-C(15B) | 179.6(7) |
| C(13B)-N(1B)-C(14B)-C(16B) | −56.2(9) |
| C(12B)-N(1B)-C(14B)-C(16B) | 177.6(7) |
| N(1B)-C(13B)-C(15B)-C(17B) | −56.5(10) |

TABLE 5-continued

Torsion angles [°] for the 1-[3-[3-(4-chlorophenyl)propoxy]propyl]-piperidine monohydrochloride crystal

| | |
|---|---|
| N(1B)-C(14B)-C(16B)-C(17B) | 54.4(10) |
| C(14B)-C(16B)-C(17B)-C(15B) | −54.9(10) |
| C(13B)-C(15B)-C(17B)-C(16B) | 55.8(10) |

X-ray diffraction pattern is shown in FIG. 1. Characteristic peaks (2θ) of crystalline 1-[3-[3-(4-chlorophenyl)propoxy]propyl]-piperidine monohydrochloride are 11.2°, 19.9°, 20.7° and 34.1° (±0.2°); additional characteristic peaks are 11.2°, 15.4°, 16.3°, 16.9°, 17.8°, 19.9°, 20.7°, 21.0°, 21.8°, 22.6°, 24.5°, 24.6°, 25.0°, 25.5°, 26.3°, 28.3°, 30.3°, 34.1°, 35.8°, 40.0°, 46.0° (±0.2°).

Example 4

Determination of Solubility, and Stability to Oxidation Conditions of Crystalline 1-[3-[3-(4-chlorophenyl)propoxy]propyl]-piperidine Monohydrochloride, Hydrogen Oxalate, Hydrogen Succinate and Hydrogen Maleate Salts Solubility of 1-[3-[3-(4-chlorophenyl)propoxy]propyl]-piperidine monohydrochloride, hydrogen oxalate, hydrogen succinate and hydrogen maleate salts was carried out under different conditions: water at room temperature, pH 4.5 and pH 7.4, which pretends to simulate the gastric media and intestinal media respectively. Results are shown in Table 6.

TABLE 6

Solubility data.

| | Solubility (% w/v) | | |
|---|---|---|---|
| Salt | Water room T | pH 4.5 | pH 7.4 |
| Monohydrochloride | >100 | >100 | >100 |
| Hydrogen oxalate | 1-3 | 1-3 | 3-10 |
| Hydrogen succinate | >100 | >100 | >100 |
| Hydrogen maleate | >50 | >50 | 10-50 |

The results show that solubility of monohydrochloride and hydrogen succinate salts are much higher than those of hydrogen oxalate and hydrogen maleate salts.

Melting points of the above salts were also determined under nitrogen and oxygen atmosphere, in order to verify their stability to oxidation conditions.

The four salts kept substantially unchanged their melting points independently of the oxidation conditions, therefore all of them are equally stable.

Nevertheless, the low melting point of hydrogen succinate and hydrogen maleate salts made them less suitable for industrial application than monohydrochloride salt, due to a low melting point makes difficult the dry operations, also at moderate temperatures. Results are shown in Table 7.

TABLE 7

Melting points.

| Conditions | Monohydrochloride | Hydrogen oxalate | Hydrogen succinate | Hydrogen maleate |
|---|---|---|---|---|
| N₂ atmosphere | 117.68° C. | 149.16° C. | 63.21° C. | 90.85° C. |
| O₂ atmosphere | 117.54° C. | 149.28° C. | 63.46° C. | 90.74° C. |

In conclusion, monohydrochloride salt shows not only better solubility profile than other salts (hydrogen oxalate and hydrogen maleate), but also it shows better stability to oxidation conditions than hydrogen succinate and hydrogen maleate. Therefore, the combination of all of these properties made, unforeseeably, the monohydrochloride salt would be the preferred salt for its use as a pharmaceutical ingredient.

Example 5

Primary Pharmacological Actions at Histamine H3 Receptors

1-[3-[3-(4-chlorophenyl)propoxy]propyl]-piperidine monohydrochloride is a highly selective and potent human H3-receptor (H3R) inverse agonist (antagonist). Its profile has been investigated using various in vitro assays to establish its particular receptor H3 receptor inverse agonist properties.

The H3R (G-protein-coupled receptor) possesses constitutive activity, that is spontaneous activity in the absence of agonist, both in native and recombinant receptor assay systems [Rouleau et al., Brit. J. Pharmacol., 2002, 135: 383-392]. In the absence of endogeneous ligand or agonist, a proportion of the receptor population undergoes spontaneous allosteric transition, leading to a conformation that can bind G-proteins. H3R constitutive activity controls histaminergic neuron activity by reducing histamine release. Using functional assays, it has been shown that prototypic antagonists such as thioperamide and ciproxifan were in fact acting as inverse agonists. Inverse agonists achieve their effects by stabilizing an inactive state of the receptor at the expense of the activated state. Thus, they lower the level of constitutive receptor activity, resulting in activation of histaminergic neurons. In contrast, neutral antagonists combine equally with both conformations of the receptor and do not affect basal activity.

Histamine H3 Receptor Binding

Determination of the affinity constants of 1-[3-[3-(4-chlorophenyl)propoxy]propyl]-piperidine monohydrochloride for the H3R was performed on mouse brain cortex membranes and on recombinant human H3 receptors expressed in various mammalian cells. Table 8 summarizes the Ki values observed in the different systems.

TABLE 8

1-[3-[3-(4-chlorophenyl)propoxy]propyl]-piperidine monohydrochloride Binding Affinities to the H3 Histamine Receptor

| Radioligand | Mouse Brain native H3R Ki (nM) | Human Recombinant H3R* Ki (nM) |
|---|---|---|
| [$^3$H](R)α-MeHA | 5.7 ± 0.2 | ND |
| [$^3$H]N$^\alpha$methylhistamine | ND | 1.0 ± 0.1 |
| [$^{125}$I]iodoproxyfan | 14 ± 0.1 | 2.4 ± 0.5 |

[$^3$H](R)α-MeHA: [$^3$H](R)α-methylhistamine.
ND: not determined.
*expression in rat glioma C6 cells.

From these results, 1-[3-[3-(4-chlorophenyl)propoxy]propyl]-piperidine monohydrochloride appeared to be about 6 times more potent at the human H3R as compared to the mouse H3R in the same test system.

Selectivity of 1-[3-[3-(4-chlorophenyl)propoxy]propyl]-piperidine monohydrochloride at Histamine Receptors A difference of three orders of magnitude was shown between the affinity at H3R and at other histamine receptors (Table 9)

TABLE 9

Binding affinities of 1-[3-[3-(4-chlorophenyl)propoxy]propyl]-piperidine monohydrochloride at Other Histamine Receptors

| | Receptors | | | |
|---|---|---|---|---|
| Test System | Human H1R [$^3$H]mepyr. | [$^{35}$S]GTPγS | H2R [$^{125}$I]iodoamino-potentidine | Human H4R [$^3$H]histamine binding assay |
| Ki or IC$_{50}$ | 1.14 μM | >10 μM | ≈5 μM | >>100 μM |

[$^{35}$S]GTPγS: Histamine-Induced increase in [$^{35}$S]GTPγS binding.
[$^3$H]mepyr.: Specific [$^3$H]mepyramine binding at recombinant human H1 receptors expressed in HEK293 cells.
[$^{125}$I]iodoamino-potentidine binding assay to the guinea pig H2 receptor.

Histamine H3 Receptor-Mediated Response

A23187 Ionophore-Evoked Release of [$^3$H]Arachidonic Acid:

The maximal effect of 1-[3-[3-(4-chlorophenyl)propoxy]propyl]-piperidine monohydrochloride on the ionophore A23187-evoked [$^3$H]arachidonic acid (AA) release from CHO cells expressing the rat or the human H3R at levels of 300-400 fmol/mg protein was studied according to Morisset et al. [Nature, 2000, 408, 860-864].

In the rat recombinant system, 1-[3-[3-(4-chlorophenyl)propoxy]propyl]-piperidine monohydrochloride (1 μM) reduced a 40% decrease (similar to that exerted by a 1 μM concentration of ciproxifan) of the A23187-evoked [$^3$H]AA release.

In the human recombinant system, 1-[3-[3-(4-chlorophenyl)propoxy]propyl]-piperidine monohydrochloride (1 μM) reduced by 20% the A23187-evoked [3H]AA release (i.e. to the same extent as the reduction exerted by a 1 μM concentration of ciproxifan).

The potent effect of 1-[3-[3-(4-chlorophenyl)propoxy]propyl]-piperidine monohydrochloride in both experiments demonstrated its strong inverse agonist activity.

[$^{35}$S]GTPγS Specific Binding to Human H3 Receptor:

The effect of 1-[3-[3-(4-chlorophenyl)propoxy]propyl]-piperidine monohydrochloride on the [$^{35}$S]GTPγS specific binding to membranes preparation from CHO cells expressing the human H3R at different levels was also studied. At a level of 410 fmol/mg protein, 1-[3-[3-(4-chlorophenyl)propoxy]propyl]-piperidine monohydrochloride decreased in a concentration-dependent manner the specific binding of [$^{35}$S]GTPγS with an EC$_{50}$ value of 1.5±0.1 nM and a maximal decrease of 25%. 1-[3-[3-(4-chlorophenyl)propoxy]propyl]-piperidine monohydrochloride caused a more potent maximal inhibition than that induced by ciproxifan, an inverse agonist analogue (1 μM; 17% decrease).

At a higher receptor expression level (1000-1100 fmol/mg protein), 1-[3-[3-(4-chlorophenyl)propoxy]propyl]-piperidine monohydrochloride presented similar effects. 1-[3-[3-(4-chlorophenyl)propoxy]propyl]-piperidine monohydrochloride (10 nM) induced a 22% decrease in [$^{35}$S]GTPγS specific binding, an effect clearly higher than the 16% reduction caused by 1 μM ciproxifan. This indicates that 1-[3-[3-(4-chlorophenyl)propoxy]propyl]-piperidine monohydrochloride behaves as a potent inverse agonist with a high intrinsic activity.

In addition, 1-[3-[3-(4-chlorophenyl)propoxy]propyl]-piperidine monohydrochloride shifts the H3 agonist imetit-induced increase in [$^{35}$S]GTPγS specific binding to membranes of HEK293 stably expressing the human H3R (#1000 fmol/mg protein). Therefore 1-[3-[3-(4-chlorophenyl)propoxy]propyl]-piperidine monohydrochloride shows the properties of a competitive H3R antagonist of high potency ($K_B$ value of 0.31 nM).

Hence, 1-[3-[3-(4-chlorophenyl)propoxy]propyl]-piperidine monohydrochloride appears as an extremely potent inverse agonist/antagonist at the human H3R in terms of both $EC_{50}$, $E_{max}$ and $K_B$ values.

Example 6

Pharmacological Evaluation of Antiepileptic Activity

The potential benefit of 1-[3-[3-(4-chlorophenyl)propoxy]propyl]-piperidine monohydrochloride in epilepsy has been evaluated in different models of seizure in rats and mice. The occurrence and duration of seizures were determined as well as their expression on the electroencephalogram (EEG) recording.

Methods: Three different animal models of epilepsy (generalized non convulsive, generalized tonic-clonic and temporal lobe seizures) have been used, as described below:

1. *Absence Epilepsy in GAERS Rat* [Danober at al., *Prog. Neurobio.*, 1998, 55, 27-57]

A strain of Wistar rats with spontaneously generalized non convulsive seizures (absence seizures) has been developed in Strasbourg (Genetic Absence Epilepsy Rats of Strasbourg or GAERS). Seizures are characterized by bilateral and synchronous spike-and-wave discharges (7-9 Hz) on EEG, concomitant with behavioral arrests. These discharges generally last about 20 sec and occur spontaneously every minute when the animals are in a state of quiet wakefulness. Pharmacological reactivity of this model is similar to human absence-epilepsy (e.g., valproate and ethosuccimide are protective). After a recovery period, implanted rats (cortical and hippocampal EEG electrodes) were recorded over a 20 min reference period. Then, 1-[3-[3-(4-chlorophenyl)propoxy]propyl]-piperidine monohydrochloride (5 mg or 20 mg/kg, i.p.) or saline were administered (n=8 per group) and the EEG recording was continued for 60 min. Rats received the alternative treatment one week later. Cumulated duration of absence-seizures was measured by 20 min periods during the two sessions. Fast Fourier transform analysis of EEG recording allowed detection of any rhythm change during both ictal and inter-ictal periods (background activity).

2. *Electroshock in Mice* [Swinyard et al., *J. Pharmacol. Exp. Ther.*, 1952, 106, 319-330]

Tonic-clonic seizures are induced in rodents by brief electrical shocks (50 Hz, 80 mA intensity, 0.2 sec duration) applied on the ears. Mice display a tonic extension and/or a tonic flexion of limbs and body followed by clonies of 15-20 sec duration. Concomitant low amplitude, high frequency activity is observed on the cortical EEG during the tonic phase, followed by a burst of spike and poly-spike discharges during the clonic phase. Electroshock-induced seizures have the same reactivity as tonic-clonic seizures in patients and are suppressed by antiepileptic drugs (AEDs) like phenytoin, phenobarbital, carbamazepine, benzodiazepines and valproate. Mice (n=8 per group) received 1-[3-[3-(4-chlorophenyl)propoxy]propyl]-piperidine monohydrochloride (100 mg/kg, p.o.) or saline. Electroshock test was applied 60 min following injection and the duration of each seizure was determined.

3. *Kainate-Induced Temporal Lobe Seizures in Mice* [Riban et al., *J. Pharmacol. Exp. Ther.*, 2002, 112, 101-111]

Unilateral injection of kainic acid (1 nmol in 50 mL) into the dorsal hippocampus in mice induces a non-convulsive status that results in spontaneous recurrent focal seizures after 2-3 weeks. Seizures (5 to 20 times per hour in quiet mice) are characterized by a behavioral arrest and/or stereotypies, concomitant with spike and poly-spike discharges recorded in the injected hippocampus. All AEDs tested in this model (valproate, carbamazepine, phenytoin, levetiracetam) are without significant effects, except benzodiazepines which transiently suppress seizures. This model reproduces the behavioral, EEG, pharmacological and histological characteristics of mesial temporal lobe epilepsy, a form of epilepsy which is often drug-resistant in humans. After a recovery period, implanted mice (for EEG recording) were injected with kainic acid. They were EEG recorded at least 3 weeks after injection for selection of animals with consistent hippocampal seizure. Then, after a 20 min reference recording period, selected mice received either 1-[3-[3-(4-chlorophenyl)propoxy]propyl]piperidine monohydrochloride (10 or 20 mg/kg, i.p.) or saline and the recording was continued for 60 min. Treatments were given in a counter balanced order (after a one week washout period between two sessions).

Summary of 1-[3-[3-(4-chlorophenyl)propoxy]propyl]-piperidine monohydrochloride in Epilepsy Models:

1-[3-[3-(4-chlorophenyl)propoxy]propyl]-piperidine monohydrochloride significantly decreased both the number and cumulated durations of spike and wave discharges in GAERS rats, 20, 40 and 60 min after administration of the product (20 mg/kg, i.p.). Cumulated duration of spike-and-wave discharges was reduced by 25 and 77% at doses of 5 and 20 mg/kg, respectively, as compared to saline ($p<0.05$, vs. saline).

In the maximal electroshock seizure model, a complete protection was observed.

In kainite-induced hippocampal seizures in mice, 1-[3-[3-(4-chlorophenyl)propoxy]propyl]-piperidine monohydrochloride (10 mg/kg, i.p.) reduced the cumulated duration and the number of hippocampal discharges during the first 40 min after administration ($p<0.05$ vs. saline). At the doses of 20 mg/kg i.p., the cumulated duration of hippocampal discharges was also reduced ($p<0.05$, at 60 min).

The antiepileptic effects of 1-[3-[3-(4-chlorophenyl)propoxy]propyl]-piperidine monohydrochloride were not associated with significant change in EEG background activity, as revealed by spectral analysis of the inter-ictal periods.

Example 7

Pharmacodynamic Interactions with Antiepileptic Drugs (AEDs)

Since the clinical indication for 1-[3-[3-(4-chlorophenyl)propoxy]propyl]-piperidine is epilepsy, the interactions with antiepileptic drugs (AEDs) have been studied.

AEDs Interaction on the Rotarod Test in the Mouse

The aim of this work was to investigate possible pharmacodynamic interactions following the coadministration of 1-[3-[3-(4-chlorophenyl)propoxy]propyl]-piperidine monohydrochloride with various antiepileptic and other GABA-acting drugs in a standardized model of motor coordination, namely the rotarod test in the mouse.

Methods: 1-[3-[3-(4-chlorophenyl)propoxy]propyl]-piperidine monohydrochloride (10 mg/kg), carbamazepine (25 mg/kg), sodium valproate (200 mg/kg), phenytoin (25 mg/kg), diazepam (2 mg/kg) and phenobarbital (15 mg/kg) were intraperitoneally administered in a single dose treatment, alone and in combination with 1-[3-[3-(4-chlorophenyl)propoxy]propyl]-piperidine monohydrochloride. The coadministration of 1-[3-[3-(4-chlorophenyl)propoxy]propyl]-piperidine monohydrochloride was performed min prior to the administration of AEDs. One group of animals, which was used as control, was injected with the vehicle only.

Results show that no impairment in motor coordination was detected in the treated groups compared to control animals. Moreover, under these experimental conditions, 1-[3-[3-(4-chlorophenyl)propoxy]propyl]-piperidine monohydrochloride does not induce any pharmacodynamic interactions leading to motor incoordination when administered with the above mentioned compounds.

Conclusion: It can be concluded that the coadministration of 1-[3-[3-(4-chlorophenyl)propoxy]propyl]-piperidine monohydrochloride does not induce changes in the pattern of motor behavior reported for the antiepileptics and GABA-acting drugs.

Example 8

Sleep/Wakefulness and Electroencephalogram (EEG) and Electromyogram (EMG) Effects The effects of 1-[3-[3-(4-chlorophenyl)propoxy]propyl]-piperidine monohydrochloride on sleep-wake cycle control have been investigated in freely moving cats and mice.

Methods: A similar experiment approach was used in both cat and mouse studies. Animals were chronically implanted with cortical and muscle electrodes to record EEG and EMG respectively, to allow monitoring their sleep-wake cycle. After recovery from surgery, animals were housed individually in a sound-proof recorded room maintaining at appropriate ambient temperature on a 12 h light/dark cycle. Polygraphic recordings were performed during 4 days to collect reference qualitative and quantitative data of sleep-wake control in each individual. Then, pharmacological evaluation was performed over 24 h sessions and analyzed by successive 30 sec epochs. Wakefulness and sleep states were identified as previously described for cats [Petitjean et al., *Brain Res.*, 1975, 88: 439-53] and mice [Valatx and Bugat, *Brain Res.*, 1974, 69: 315-30].

1. Sleep-Wake Cycle Study in Cats

Polygraphic recordings were started 7 days after surgery. Sleep-wake recording criteria included wakefulness (W), light slow wave sleep (SWS1), deep SWS (SWS2) and paradoxical sleep (PS). Spectral analysis of EEG was performed by Fast-Fourier Transform in the frequency bands 0.8-2.5 Hz ($\delta$ slow waves), 8-15 Hz (spindles) and 20-45 Hz ($\beta$ and $\gamma$ rapid waves). The 1-[3-[3-(4-chlorophenyl)propoxy]propyl]-piperidine monohydrochloride compound was administered orally at doses of 5 or 10 mg/kg.

2. Sleep-Wake Cycle Study in Mice

Polygraphic recordings were started 15 days after surgery (5 days recovery plus 10 days acclimation to the recording wires). Sleep-wake recording criteria included wakefulness (W), slow wave sleep (SWS) and paradoxical sleep (PS). Spectral analysis of EEG was performed by Fast-Fourier Transform in the 0.8-2.5 Hz, 8-15 Hz and 30-60 Hz frequency bands. The 1-[3-[3-(4-chlorophenyl)propoxy]propyl]-piperidine monohydrochloride compound was administered orally at 2.5, 5, 10 or 20 mg/kg.

Results

In cats, oral administration of 1-[3-[3-(4-chlorophenyl)propoxy]propyl]-piperidine monohydrochloride caused a dose-dependent increase in awakening at the expense of SWS, in particular SW2, and of PS. At 10 mg/kg, the waking effect occurred as early as the first hour after treatment, animals being almost permanently wakeful for 6-12 h. The potency of the wakening effect of the product was confirmed in the spectral analysis of neocortical EEG. Indeed, decrease/suppression of slow waves ($\delta$, 0.8-2.5 Hz) and 8-15 Hz were observed. No major change in the animal behavior was observed after treatment.

In mice, oral administration of 1-[3-[3-(4-chlorophenyl)propoxy]propyl]-piperidine monohydrochloride caused similar dose-dependent increase in awakening (W). This effect took place at the expense of SWS and PS. This effect was confirmed by a decrease/suppression of slow $\delta$ waves and 8-15 Hz spindles and a strong increase in fast rhythms ($\beta$ and $\gamma$ frequencies) of the EEG spectral analysis. No behavioral change was observed in treated mice.

Significant increases in W duration were observed in both animal species treated with 1-[3-[3-(4-chlorophenyl)propoxy]propyl]-piperidine monohydrochloride. In cats, 10 mg/kg of the product caused a 79% increase in W duration during a 6 h recording period ($p<0.01$). Similar results were observed in mice treated with 10 and 20 mg/kg of the product (29 and 69% increase, respectively, $p<0.01$).

Conclusion: These results demonstrate that 1-[3-[3-(4-chlorophenyl)propoxy]propyl]-piperidine monohydrochloride markedly increased the duration of waking in two animal species. Moreover, the EEG results suggest that this compound could improve the quality of awakening, e.g. by reinforcing the level of vigilance and attention, in the absence of any noticeable behavioral change.

Example 9

Effects on Learning

The precognitive effects of 1-[3-[3-(4-chlorophenyl)propoxy]propyl]-piperidine monohydrochloride were investigated in mice in the two-trial object recognition paradigm. This learning and memory paradigm is based on spontaneous exploratory activity of rodents and has been shown to be sensitive to the effects of ageing and cholinergic dysfunction [Scali et al., *Neurosci. Lett.*, 1994, 170, 117-120; Bartolini et al., *Biochem. Nehav.*, 1996, 53, 277-283].

1. Effect of 1-[3-[3-(4-chlorophenyl)propoxy]propyl]-piperidine monohydrochloride on the Scopolamine-Induced Learning Deficit Methods: Mice were allowed to explore a box for 30 min in the presence of two objects. The day after, mice were submitted to two trials spaced by an interval of 60 min. During the first trial (T1), mice were placed in the box containing the two identical objects and the time required by each animal to complete 20 sec of object exploration was determined. Exploration was considered to be directing the nose at a distance closer than 2 cm to the object and/or touching the object. For the second trial (T2), one of the objects presented in the first trial was replaced by and unknown novel object. Mice were placed in the box for 5 min and exploration of each object together with motor activity was determined. The following parameters were measured.

Time required to achieve 20 s of object exploration on T1,
Time spent in active exploration of the familiar object on T2,
Time spent in active exploration of the novel object on T2,
Motor activity on T2.

The ability of 1-[3-[3-(4-chlorophenyl)propoxy]propyl]-piperidine monohydrochloride (5 and 15 mg/kg, i.p., 40 min before challenge) to reverse experimental amnesia induced by the scopolamine (0.3 mg/kg, i.p., 30 min before challenge) was investigated.

Results: The scopolamine-induced amnesia is significantly ($p=0.0056$) reversed by 1-[3-[3-(4-chlorophenyl)propoxy]propyl]-piperidine monohydrochloride at the dose of 15 mg/kg. At the lower dose (5 mg/kg) a reversal trend appeared without being significant. In addition, the increase in the motor activity observed in scopolamine-treated mice is not significantly modified by the product. The 5 mg/kg dose did not modify the time for mice to reach the learning criteria on the first trial whereas this time it was significantly increased at the higher dose.

2. Effect of 1-[3-[3-(4-chlorophenyl)propoxy]propyl]-piperidine monohydrochloride on "Natural" Forgetting Methods: Mice were submitted to the first trial (T1), placed in the box containing two identical objects and the time required by each animal to complete 8 sec of object exploration was determined. Exploration was considered to be directing the nose at a distance closer than 2 cm to the object and/or touching the object. Immediately after the first trial mice were treated with the vehicle or tacrine (0.25 mg/kg, i.p.). Three hours later the second trial (T2) was performed introducing the mouse in the box with one of the objects presented in the first trial replaced by an unknown novel object. Mice were placed in the box for 5 min and exploration of each object together with motor activity was determined. The following parameters were measured:

Time required to achieve 8 s of object exploration on T1,
Time spent in active exploration of the familiar object on T2,
Time spent in active exploration of the novel object on T2,
Motor activity on T2.

The ability of 1-[3-[3-(4-chlorophenyl)propoxy]propyl]-piperidine monohydrochloride (15 mg/kg, i.p., 30 min before T1) to modulate the natural forgetting in the presence or absence of the tacrine treatment was investigated.

Results: The duration of the acquisition phase (T1) was reduced to 8 sec of object exploration as compared to the duration of this phase (20 sec) retained in the scopolamine-induced amnesia model. In these conditions, the duration of the T1 in the treated mice was significantly increased as compared to control mice. In spite of a shorter acquisition phase, the "natural" forgetting is significantly reduced by 1-[3-[3-(4-chlorophenyl)propoxy]propyl]-piperidine monohydrochloride at the dose of 15 mg/kg and by tacrine without change in the tacrine effect when the acetylcholinesterase inhibitor is associated together with the H3 receptors antagonist/inverse agonist. In addition, a slight increase in the motor activity was observed in treated mice.

These observations of a reversal produced by 1-[3-[3-(4-chlorophenyl)propoxy]propyl]-piperidine monohydrochloride of the "natural" forgetting and of the learning deficit elicited by scopolamine are consistent with a large variety of observations gathered with other H3 receptors antagonists/inverse agonists, including the prototypical drug thioperamide.

Example 10

Animal Toxicology and Safety Pharmacology

Acute Toxicity in Mouse and Rat

The acute toxicity of 1-[3-[3-(4-chlorophenyl)propoxy]propyl]-piperidine monohydrochloride has been evaluated by oral and intravenous route in mice and rats.

1-[3-[3-(4-chlorophenyl)propoxy]propyl]-piperidine monohydrochloride demonstrated a good safety profile in rodents. In mice, the no-effect dose was >30 mg/kg orally and >5 mg/kg i.v., with a maximum non lethal dose of 100 mg/kg. The minimum lethal doses were 150 mg/kg p.o. and 10 mg/kg, i.v. In rat, the no-effect dose was >50 mg/kg, orally and 12 mg/kg i.v., with a maximum non lethal oral dose of 100 mg/kg (expressed as single doses).

Repeat Oral Dose Studies in Rat and Monkey

In rats, a 13-week repeat dose study showed satisfactory tolerability of 1-[3-[3-(4-chlorophenyl)propoxy]propyl]-piperidine monohydrochloride up to 30 mg/kg/day, a dose which can be defined as the NOAEL (no observed adverse effect level) in rats.

In monkeys, a 13-week repeat dose study showed no adverse effects of 1-[3-[3-(4-chlorophenyl)propoxy]propyl]-piperidine monohydrochloride up to 5 mg/kg/day. This dose was defined as the NOAEL in monkeys.

Safety Pharmacology

The ratio between the defined NOAEL in rat and monkey repeat-dose studies and the doses pharmacologically active suggests that 1-[3-[3-(4-chlorophenyl)propoxy]propyl]-piperidine monohydrochloride can act as a drug with a satisfactory safety margin.

1-[3-[3-(4-chlorophenyl)propoxy]propyl]-piperidine monohydrochloride has been found not to be genotoxic in vitro or in vivo.

Example 11

Clinical Efficacy in Epilepsy

Photosensitivity, defined as a generalized epileptiform reaction on intermittent photic stimulation (IPS) outlasting the stimulus train is found in about 5% of epileptic patients [*Kastelejin-Nolst Trenité DGA. Acta Neurol. Scand.,* 1989; 80:1-149]. Unlike most other epilepsies, photosensitive epilepsy is a reflex epilepsy and epileptiform discharges can be evoked at any time by IPS in the laboratory. By determination of both upper and lower sensitivity limits (frequencies per flash) a so-called photosensitivity range can be determined. The range is related to liability of seizures in daily life of the patient. This photosensitivity range is relatively stable within a patient and can be diminished or abolished by antiepileptic medication. Thus, the technique of using the photosensitivity range proved to be a good model to study the epileptic properties of a single dose of an experimental drug in humans.

Hence, the goal of this single-blind study was to evaluate the antiepileptic effect of 1-[3-[3-(4-chlorophenyl)propoxy]propyl]-piperidine monohydrochloride (single dose) in this human model predictive of generalized absence epilepsy. The single blind design was chosen in order to reduce comparison bias of IPS response observed after treatment with 1-[3-[3-(4-chlorophenyl)propoxy]propyl]-piperidine monohydrochloride administration at day 2 with placebo evaluation at day 1.

Twelve patients have been enrolled. Four patients received the dose of 20 mg. Among them one patient showed total suppression of photo paroxysmal response (PPR) lasting 6 hours. Four patients received the dose of 40 mg. Among them one showed partial suppression of PPR and one total suppression of PPR. Four received the dose of 60 mg, with clinical response in all four patients. Moreover, two patients showed total suppression of PPR. The effect is appearing 1-2 hours post administration and is lasting more than 8 hours up to 36 hours (one patient, Table 10).

TABLE 10

Effect of 1-[3-[3-(4-chlorophenyl)propoxy]propyl]-piperidine monohydrochloride on PPR in epileptic patients

| Patient # | Dose | Suppression of PPR | Delay of apparition | Duration of effect | Concomitant AED(s) |
|---|---|---|---|---|---|
| 1 | 20 mg | No | — | — | Carbamazepine 400 mg |
| 2 | 20 mg | No | — | — | Topiramate 50 mg |
| 3 | 20 mg | No | — | — | None |
| 4 | 20 mg | Total | 2 hours | 6 hours | Sodium valproate 750 mg Levetiracetam 1000 mg |
| 5 | 40 mg | No | — | — | None |
| 6 | 40 mg | Total | <1 hour | >8 hours | Sodium valproate 1000 mg |
| 7 | 40 mg | Partial | 2 hours | 26 hours | Sodium valproate 1000 mg Levetiracetam 1000 mg |
| 8 | 40 mg | No | — | — | Sodium valproate 500 mg |
| 9 | 60 mg | Partial | 2 hours | >8 hours | Sodium valproate 500 mg |
| 10 | 60 mg | Total | <1 hour | >36 hours | None |
| 11 | 60 mg | Partial | <1 hour | >8 hours | Sodium valproate 1000 |
| 12 | 60 mg | Total | <1 hour | 26 hours | Lamotrigine 300 mg Levetiracetam 1000 mg |

Example 12

Interaction with Olanzapine: Analysis of Subjective Satiety

A single-center, open-label, placebo-controlled phase I study was performed to evaluate the subjective satiety in 6 volunteers. The volunteers enrolled in the study underwent five single day administration periods. They received placebo in period 1, olanzapine 5 mg in period 2, 1-[3-[3-(4-chlorophenyl) propoxy]propyl]-piperidine monohydrochloride 60 mg in period 3, olanzapine 5 mg+1-[3-[3-(4-chlorophenyl) propoxy]propyl]-piperidine monohydrochloride 60 mg in period 4 and olanzapine 2.5 mg+1-[3-[3-(4-chlorophenyl) propoxy]propyl]-piperidine monohydrochloride 60 mg in period 5.

Significant treatment effect was elicited for hunger sensation, desire to eat and prospective consumption.

Compared to placebo, subjective satiety is significantly decreased after 5 mg of olanzapine. This effect can be correlated to the well established weight gain in patients treated with olanzapine. Comparison of subjective satiety after 1-[3-[3-(4-chlorophenyl)propoxy]propyl]-piperidine monohydrochloride 60 mg versus placebo is significantly increased. The extent of satiety decrease shows a dose-response relationship. Consequently, subjective satiety is statistically different between both treatments, i.e. olanzapine 5 mg and 1-[3-[3-(4-chlorophenyl)propoxy]propyl]-piperidine monohydrochloride 60 mg. More importantly, the association of olanzapine 5 mg+1-[3-[3-(4-chlorophenyl)propoxy]propyl]-piperidine monohydrochloride 60 mg shows that this compound is able to counteract the effect of olanzapine leading to subjective satiety superimposable to placebo.

Example 13

Clinical Effects on Awakening and Vigilance

A single-center, double-blind, randomized, placebo-controlled, single ascending doses, electroencephalographic study was performed in 36 volunteers. Subjects were consecutively enrolled in groups 1 to 6 (1, 5, 10, 20, 40 or 60 mg). All subjects of each dose group were randomly assigned to receive either 1-[3-[3-(4-chlorophenyl)propoxy]propyl]-piperidine monohydrochloride or placebo, in such a way that 5 subjects received the product and one subject received placebo.

From the EEG spectral analysis performed before treatment, the study subjects could be stratified as microvolted (66%) and normo or grandvolted (33%). The distribution between those subjects with 30-40% slow activity and 20-25% rapid activity (microvolted), and those with 10% slow activity (normovolted) or 60-80% of α-activity (grandvolted), explains that before drug administration significant differences were elicited for 20-30 Hz and 30-40 Hz activities.

Two hours after single oral administration of 40 mg and 60 mg of 1-[3-[3-(4-chlorophenyl)propoxy]propyl]-piperidine monohydrochloride, a statistically significant increase of rapid activity (20-30 Hz on anterior leads and 16 to 40 Hz on the posterior leads) was elicited. Consistently, the median peak position (MPP) shifted on the frequency axis from 10 to 15-17 Hz and from 11 to 13-15 Hz. The increase of rapid activities was at the expense of the α-activity on the posterior leads. Four hours after administration, an increase of rapid activity (20-30 Hz) was still present, while α-activity did not return to pre-dose value. Overall, these modifications, which are consistent with previous animal findings, characterize a profile of drug activity that improves awakening and cognitive activities.

Psychometric and vigilance tests were also performed in this study to assess any possible impairment. Overall, there was no statistically significant drug effect on self-perception of sleep (LEEDS), alertness, contentedness and calmness (Bond-Lader VAS) and choice reaction time (CRT). In addition, this study has shown that there was no trend or statistically significant drug effect on the ARCI 49.

In contrast, there was a statistically significant drug effect on the flicker, the fusion and the flicker-fusion thresholds (CFF) that were higher after administration of single 60 mg 1-[3-[3-(4-chlorophenyl)propoxy]propyl]-piperidine monohydrochloride than after administration of placebo. These results indicate that single oral administration of 60 mg of the product increased the subject's vigilance.

Overall, these results have shown that in the conditions of the study, single oral administration of 40 mg and 60 mg 1-[3-[3-(4-chlorophenyl)propoxy]propyl]-piperidine monohydrochloride induced an increase of rapid activity of the EEG consistently with an increase of subject's vigilance as elicited by the results of the Flicker-Fusion test.

Example 14

20 mg Coated Tablets

| | |
|---|---|
| 1-[3-[3-(4-chlorophenyl)propoxy]propyl]-piperidine monohydrochloride | 20 mg |
| Colloidal silicon dioxide | 1 mg |
| Crospovidone | 10 mg |
| Talc | 10 mg |
| Magnesium stearate | 3 mg |
| Microcrystalline cellulose, | 81 mg |
| Total weight | 125 mg |

Example 15

20 mg Coated Tablets

| | |
|---|---|
| 1-[3-[3-(4-chlorophenyl)propoxy]propyl]-piperidine monohydrochloride | 20 mg |
| Starch | 10 mg |
| Stearic acid | 1 mg |
| Mannitol | 15 mg |
| Lactose | 79 mg |
| Total weight | 125 mg |

Example 16

40 mg Coated Tablets

| | |
|---|---|
| 1-[3-[3-(4-chlorophenyl)propoxy]propyl]-piperidine monohydrochloride | 40 mg |
| Colloidal silicon dioxide | 1 mg |
| Crospovidone | 10 mg |
| Talc | 10 mg |
| Magnesium stearate | 3 mg |
| Silicified microcrystalline cellulose | 61 mg |
| Total weight | 125 mg |

Example 17

40 mg Coated Tablets

| | |
|---|---|
| 1-[3-[3-(4-chlorophenyl)propoxy]propyl]-piperidine monohydrochloride | 40 mg |
| Colloidal silicon dioxide | 1 mg |
| Crospovidone | 10 mg |
| Talc | 3.75 mg |
| Magnesium stearate | 1.25 mg |
| Silicified microcrystalline cellulose | 34.50 mg |
| Microcrystalline cellulose | 34.50 mg |
| Total weight | 125 mg |
| Coating excipients, enough quantity to obtain a uniform coating comprising the following components: | 8 mg |
| Butylated methacrylate copolymer | |
| Soldium lauryl sulfate | |
| Stearic acid | |
| Talc | |
| Titanium dioxide | |
| Magnesium stearate | |
| Purified water | |
| Total weight (film coated tablets) | 133 mg |

The invention claimed is:

1. Crystalline 1-[3-[3-(4-chlorophenyl)propoxy]propyl]-piperidine monohydrochloride of formula (I)

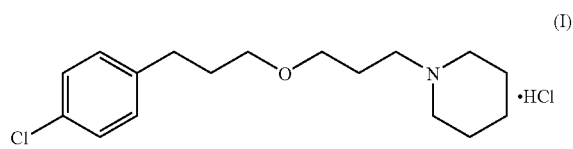

(I)

optionally comprising water up to 6%, and having an X-ray diffractogram that comprises characteristic peaks (2θ) at 11.2°, 19.9°, 20.7° and 34.1° ±0.2°

2. The crystalline 1-[3-[3-(4-chlorophenyl)propoxy]propyl]-piperidine monohydrochloride according to claim 1, having an X-ray diffractogram that comprises characteristic peaks (2θ) at 11.2°, 15.4°, 16.3°, 16.9°, 17.8°, 19.9°, 20.7°, 21.0°, 21.8°, 22.6°, 24.5°, 24.6°, 25.0°, 25.5°, 26.3°, 28.3°, 30.3°, 34.1°, 35.8°, 40.0°, 46.0° ±0.2°.

3. A process for the production of the compound according to claim 1 comprising:
  a) reacting 1-[3-[3-(4-chlorophenyl)propoxy]propyl]-piperidine with a reactant selected from hydrogen chloride or hydrochloric acid in a suitable solvent and isolating the precipitated 1-[3-[3-(4-chlorophenyl)propoxy]propyl]-piperidine monohydrochloride; and
  b) crystallizing the precipitated 1-[3-[3-(4-chlorophenyl)propoxy]propyl]-piperidine monohydrochloride in a suitable solvent.

4. The process of claim 3 wherein the reactant is hydrogen chloride.

5. The process of claim 4 wherein the hydrogen chloride is added as gaseous hydrogen chloride.

6. The process of claim 3, wherein the suitable solvent of step a) is selected from the group consisting of acetone, methanol, ethanol, propanol, water, ethyl acetate, i-propanol, butanol, i-butanol, s-butanol, t-butanol, hexane, toluene, t-butyl-methyl ether, trichloroethane, and mixtures thereof.

7. The process of claim 6 wherein the suitable solvent is ethyl acetate.

8. The process of claim 3 wherein the suitable solvent of step b) is selected from the group consisting of acetone, methanol, ethanol, propanol, water, ethyl acetate, i-propanol, butanol, i-butanol, s-butanol, t-butanol, hexane, toluene, t-butyl-methyl ether, trichloroethane, and mixtures thereof.

9. The process of claim 8 wherein the suitable solvent is a mixture of ethyl acetate and i-propanol.

10. A pharmaceutical composition comprising a therapeutically effective amount of the compound as defined in claim 1, together with pharmaceutically acceptable excipients or carriers.

* * * * *

UNITED STATES PATENT AND TRADEMARK OFFICE

(12)          CERTIFICATE EXTENDING PATENT TERM
UNDER 35 U.S.C. § 156

| | | | |
|---|---|---|---|
| (68) | PATENT NO. | : | 8,207,197 |
| (45) | ISSUED | : | June 26, 2012 |
| (75) | INVENTOR | : | Raga et al. |
| (73) | PATENT OWNER | : | Bioprojet Pharma |
| (95) | PRODUCT | : | WAKIX® (pitolisant hydrochloride) |

This is to certify that an application under 35 U.S.C. § 156 has been filed in the United States Patent and Trademark Office, requesting extension of the term of U.S. Patent No. 8,207,197 based upon the regulatory review of the product WAKIX® (pitolisant hydrochloride) by the Food and Drug Administration. According to United States Patent and Trademark Office records, the original expiration date of the patent as of the date of issuance of this certificate is February 25, 2029. Because it appears that the requirements of the law have been met, this certificate extends the term of the patent for the period of

(94)                                375 days subject to the payment of maintenance fees as provided by law, with all rights pertaining thereto as provided by 35 U.S.C. § 156.

I have caused the seal of the United States Patent and Trademark Office to be affixed this 6th day of October 2022.

Kathi Vidal

Katherine K. Vidal
Under Secretary of Commerce for Intellectual Property and Director of the United States Patent and Trademark Office